United States Patent [19]

Soma et al.

[11] 4,357,323
[45] Nov. 2, 1982

[54] POLYSACCHARIDE RBS SUBSTANCE AND ANTITUMOR AGENT CONTAINING SAME

[75] Inventors: Eichi Soma; Kohei Kobayashi; Takuro Karakawa; Shigeyoshi Kato, all of Tokyo; Kiichi Uchida, Fujisawa, all of Japan

[73] Assignees: Sapporo Breweries Limited, Tokyo; Etsuo Ito, Urasoe; Daicel Chemical Industries, Ltd., Sakai, all of Japan

[21] Appl. No.: 174,536

[22] Filed: Aug. 1, 1980

[30] Foreign Application Priority Data

Aug. 13, 1979 [JP] Japan ................ 54-102216

[51] Int. Cl.$^3$ ............... C08B 37/00; A61K 31/73
[52] U.S. Cl. .................. 424/180; 424/177; 260/112 R; 260/112.5 R; 536/1; 536/18; 536/55.1
[58] Field of Search ............ 424/180, 177; 536/1, 536/18; 260/112.5 R, 112 R

[56] References Cited

U.S. PATENT DOCUMENTS

| | | | |
|---|---|---|---|
| 4,090,016 | 5/1978 | Tsuji et al. | 536/1 |
| 4,152,170 | 5/1979 | Nagase et al. | 536/1 |
| 4,221,907 | 9/1980 | Nair et al. | 536/1 |

OTHER PUBLICATIONS

Srinivasa, "Chem. Abst.", vol. 77, p. 60497(s), 1972.
Vijayagopalan, et al., "Chem. Abst.", vol. 77, p. 60504(s), 1972.
Kurup, et al., "Chem. Abst.", vol. 82, p. 109047(q), 1975.

*Primary Examiner*—Johnnie R. Brown
*Attorney, Agent, or Firm*—Frishauf, Holtz, Goodman & Woodward

[57] ABSTRACT

A polysaccharide RBS substance having the ultraviolet absorption spectrum depicted in FIG. 1 and the infrared absorption spectrum depicted in FIG. 2 is obtained from rice bran by extraction with hot water. These substances have been tested for anti-tumor activity against Sarcoma 180 ascites tumor and against Ehrlich ascites tumor and were determined to have anti-tumor activity against these tested tumors.

2 Claims, 2 Drawing Figures

POLYSACCHARIDE RBS SUBSTANCE AND ANTITUMOR AGENT CONTAINING SAME

BACKGROUND OF THE INVENTION

1. Field of the Invention

This invention relates to a novel polysaccharide RBS substance and antitumor agent containing said substance as the effective component.

2. Description of the Prior Art

As is known in the art, polysaccharides are obtained from various sources, for example, Basidiomycetes (Japanese Patent Kokai Koho No. 94012/1978), bacteria (Japanese Patent Kokai Koho No. 76896/1979), mould (Japanese Patent Publication No. 59097/1978), algae (Janese Patent Kokai Koho No. 28923/1977), and grains (Japanese Patent Kokai Koho No. 139713/1978).

It is also known that these polysaccharides have antitumor activity. However, various problems, for example, low yields, complicated production process, toxicity, etc., are encountered in using such polysaccharides as an antitumor agent.

SUMMARY OF THE INVENTION

This invention relates to a novel polysaccharide RBS substance and antitumor agent containing said substance as the effective component.

It has now been discovered that a novel polysaccharide RBS substance can be obtained from rice bran by extraction with hot water.

DETAILED DESCRIPTION OF THE INVENTION

Figure 1:
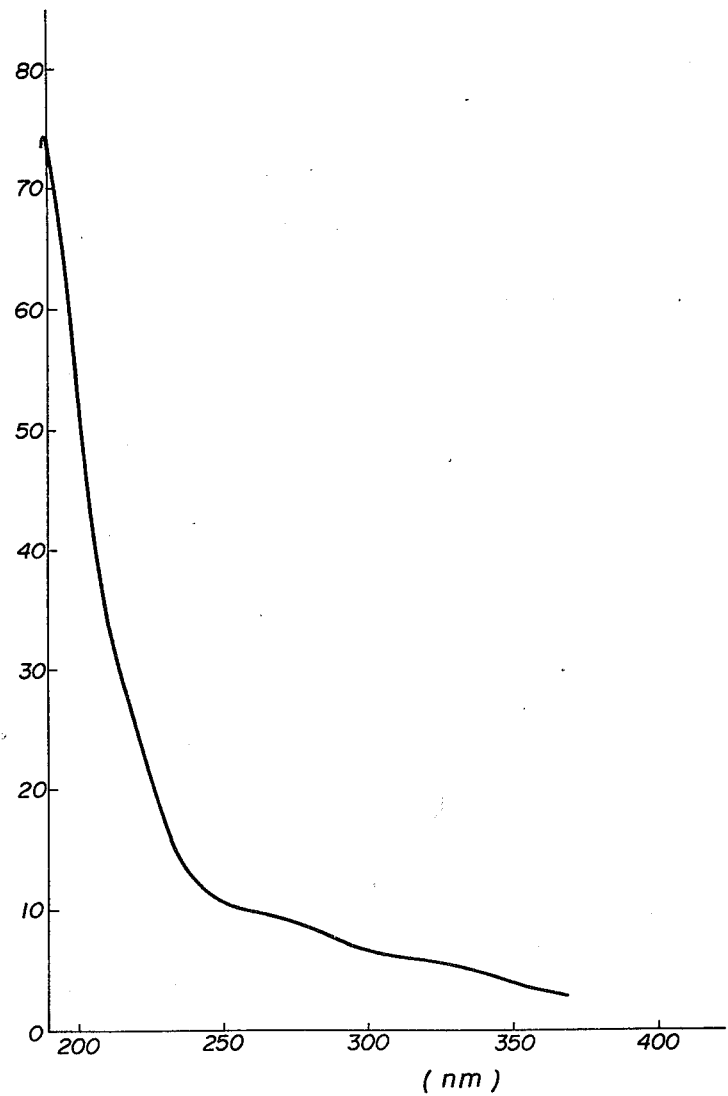
FIG. 1 is an ultraviolet absorption spectrum of the RBS substance having antitumor activity.

This invention relates to a novel polysaccharide RBS substance and antitumor agent containing said substance as the effective component.

The polysaccharide RBS substance of this invention is obtained from rice bran by extraction and purification. This rice bran is a by-product obtained in the production of polished rice from unpolished rice, and it is not limited by the variety of the unpolished rice, the producing district, the degree of polishing rate, etc. Prior to the extraction and purification of the polysaccharide RBS substance from the rice bran, it is desirable to fully wash the rice bran in order to eliminate the pulverized (or crushed) rice and other impurities. Those rice brans which have already been used for other purposes, such for example as delipid rice bran, which is a residue after extraction of rice-bran oil from rice bran, can be used in this invention.

The polysaccharide RBS substance of this invention is produced by adding organic solvents or salting-out agents to an extract obtained by hot water-treatment of rice bran to provide precipitates and, if desired, dissolving the obtained precipitates in water to purify them.

The rice bran is passed through a separator, for example, a screen, to remove impurities and is washed with water, if necessary, after pulverization. It is desirable to remove a lipid soluble fraction by use of organic solvents, such as ethyl acetate, carbon tetrachloride, chloroform, ether, n-hexane, benzene, petroleum ether, acetone etc.

The hot water-treatment of the rice bran is carried out by feeding rice bran and distilled or purified water in amount of about 5–10 times to that of the rice bran to a vessel or a pressure vessel, such for example as a stainless steel tank, an enameled tank, a glass tank, a flow system tubular extraction device and the like with or without stirring under the conditions of pressure of from 0 to 15 $Kg/cm^2$, preferably from 0 to 5.0 $Kg/cm^2$ and a temperature of from 70° C. to 200° C., preferably from 100° C. to 150° C. for 10 minutes to 24 hours, preferably 0.5 to 5 hours. Practically it is suitable to carry out the hot water-treatment at a pressure of from 0 to 3.0 $Kg/cm^2$ and a temperature of from 100° C. to 140° C. for 1 to 5 hours.

The extract obtained by the hot water-treatment is subjected to operations such as filtration, centrifugation, etc. to separate solids and, if necessary, is then concentrated to an appropriate volume by applying such means as concentration at reduced pressure, ultrafiltration, etc., singly or in combination with each other.

By collecting precipitates formed by adding a water-soluble polar organic solvent or a salting-out agent to the extract, a crude polysaccharide RBS substance is obtained.

Polar organic solvents which can be used in this procedure include methanol, ethanol, propanol, acetone, ethyl acetate, etc. The amount of the polar organic solvent being used is determined taking into account the amount of the desired substance contained in the extract, etc. For example, in the case of ethanol, it may be added in such a manner that the ethanol concentration is 30 to 50% (v/v). The formed precipitates are preferably washed with the organic solvent as described above, for example, ethanol, etc.

Salting-out agents which can be used in the above procedure include sodium chloride, ammonium sulfate, potassium chloride, barium hydroxide and barium carbonate. The salting-out agent is usually added until the degree of saturation reaches 0.5 to 1 to thereby form precipitates.

The purification of the polysaccharide RBS substance can be carried out either prior to the addition of the organic solvent or salting-out agent to the extract or after the formation of precipitates by the addition of the organic solvent or salting-out agent followed by dissolving the precipitates in water.

For the purification treatment, various known procedures can be applied. For example, amylolytic enzyme and/or proteolytic enzyme is added to a solution containing the polysaccharide RBS substance to convert impurities existing therein, such as starch, protein, etc., into low molecular weight compounds. These low molecular weight compounds are removed at a subsequent purification step.

As such enzymes, those which are produced or available on the market can be employed. For example, an amylolytic enzyme such as α-amylase, iso-amylase, pullulanase, etc., a proteolytic enzyme such as papain, pepsin, trypsin, pronase, etc., and if necessary, other enzymes can be used. It is, however, necessary that such enzymes as glucanase, hemicellulase, etc. are excluded because they may decompose the polysaccharides. In this enzyme treatment, it is preferred that the enzyme is added in a ratio of from 1/1000 to 1/5000 of the substrate and that the treatment is carried out for 6 to 120 hours, preferably 12 to 48 hours.

Additionally, the following purification methods can be used: a method in which an inorganic or organic acid, such as glacial acetic acid, sulfuric acid, hydrochloric acid, sulfosalicyclic acid, picric acid, tannic acid, trichloroacetic acid, etc. is added to an aqueous solution containing the above described polysaccharide RBS substance in a proportion of about 0.1 to 10 wt.%, preferably about 3 to 5 wt.%. When precipitates are formed, they are removed by such operations as filtration, cetrifugation, etc. and subsequently the remaining acids, inorganic ions and low molecular fractions are dialyzed for 1 to 3 days against running water or distilled water by use of a semipermeable membrane, such as cellophane membrane, collodion membrane or the like; an ion exchange method in which a cation or anion exchanger, such as Dowex, Amberlite, Duolite, Diaion or the like, is used; an ultrafiltration method in which a membrane having a fractional molecular weight of 1,000 to 50,000 is used; reverse osmosis; gel filtration; membrane filtration; centrifugation; treatment with active carbon; concentration and a combination thereof.

These purification methods can be applied singly or in combination with each other, and such combinations and the order in which they are applied are subject to no limitations.

By freeze-drying or spray-drying an aqueous solution or suspension containing the high molecular polyssacharide RBS substance which has been purified by the above described methods, a light yellowish brown to whitish grey or white RBS substance in a powdery form can be obtained.

The thus obtained polysaccharide RBS substance has the following physical and chemical properties:

This substance does not pass through a semipermeable membrane and is insoluble in organic acids or organic solvents, for example, glacial acetic acid, alcohols such as methanol, ethanol, propanol, butanol, etc., acetone, hexane, benzene, ethyl acetate, dimethyl sulfoxide, ligroin, carbon tetrachloride, chloroform, and ethers such as diethyl ether, petroleum ether, etc., but is soluble or highly soluble in water;

A 1% aqueous solution or suspension of the present substance is neutral or slightly acidic;

The present substance has no melting point and it turns brown at 220° C. and black at 280° C. (carbonizing);

Elemental analysis shows that the present substance comprises mainly carbon, hydrogen and oxygen and contains 1% or less of nitrogen and 8% or less of ash (see Table 1);

A 1% aqueous solution or suspension of the present substance is positive in the following color reactions: phenol-sulfuric acid reaction, anthrone-sulfuric acid reaction, carbazole-sulfuric acid reaction, tryptophane-sulfuric acid reaction, cystein-sulfuric acid reaction, chromotrope-sulfuric acid reaction and Molisch reaction, and negative in the following color reaction: Elson-Morgan reaction and starch-iodine reaction;

The specific rotation of the present substance obtained in Example 17 as described later is $[\alpha]_D^{20} = +142°$ to $+145°$ ($H_2O$);

Analysis of the nitrogen component of the present substance by a Hitachi automatic amino acid analyzer (sold by Hitachi Seisaku-sho Ltd.) shows that it has the following amino acid composition: 17.3% of glutamic acid, 10.4% of alanine, 10.3% of glycine, 9.5% of aspartic acid, 9.4% of lysine, 5.9% of threonine, 5.8% of serine, 5.6% of arginine, 5.4% of valine, 5.4% of leucine, 4.5% of proline, 3.1% of histidine, 2.8% of isoleucine, 2.2% of phenylalanine, 1.3% of tyrosine, 1.2% of methionine, a trace amount of tryptophane and of cystein;

It has been confirmed that the ash component comprises Si, P, K, Na, Ca, Mg, etc. and on the ground of the fact that the RBS substance is eluted in voidvolume on gel filtration using Sephalozse 6B, it is assumed that the above elements do not exist independently as an element or compound thereof in the RBS substance, but that they exist in the state that they are bound to a skeleton of the RBS substance;

The supernatant liquid obtained by a method which comprises hydrolyzing RBS substance with 1 N sulfuric acid, at 100° C. for 3 hours and then adding barium carbonate to neutralize, is positive in the following color reactions: Molisch reaction, anthrone reaction, tryptophane-sulfuric acid reaction, cystein-sulfuric acid reaction, chromotrope-sulfuric acid reaction and the like, and slightly positive in the following color reactions: biuret reaction, ninhydrin reaction, Lowry-Folin reaction and the like;

In the above hydrolysate, glucose was always detected by thin layer chromatographic analysis. On developing with the four solvents as noted below in the thin layer chromatographic analysis of those products obtained by complete hydrolysis of the RBS substance with formic acid and sulfuric acid, no spots except for the one identified as glucose could be detected.

(1) ethyl acetate:methanol:acetic acid:water (65:15:10:10)
(2) ethyl acetate:isopropanol:water (65:23:12)
(3) isopropanol:pyridine:water:acetic acid (8:8:4:1)
(4) n-butanol:pyridine:water (6:4:3) Thus it can be concluded that the present RBS substance is a polysaccharide consisting essentially of glucose as the sugar component, and moreover, on the basis of the data obtained by periodate oxidation, Smith degradation and paper chromatographic analysis of methylated sugar, it has been assumed that the RBS substance of this invention has a 1,6-glucoside bond as a main chain with branched structure.

Figure 2:
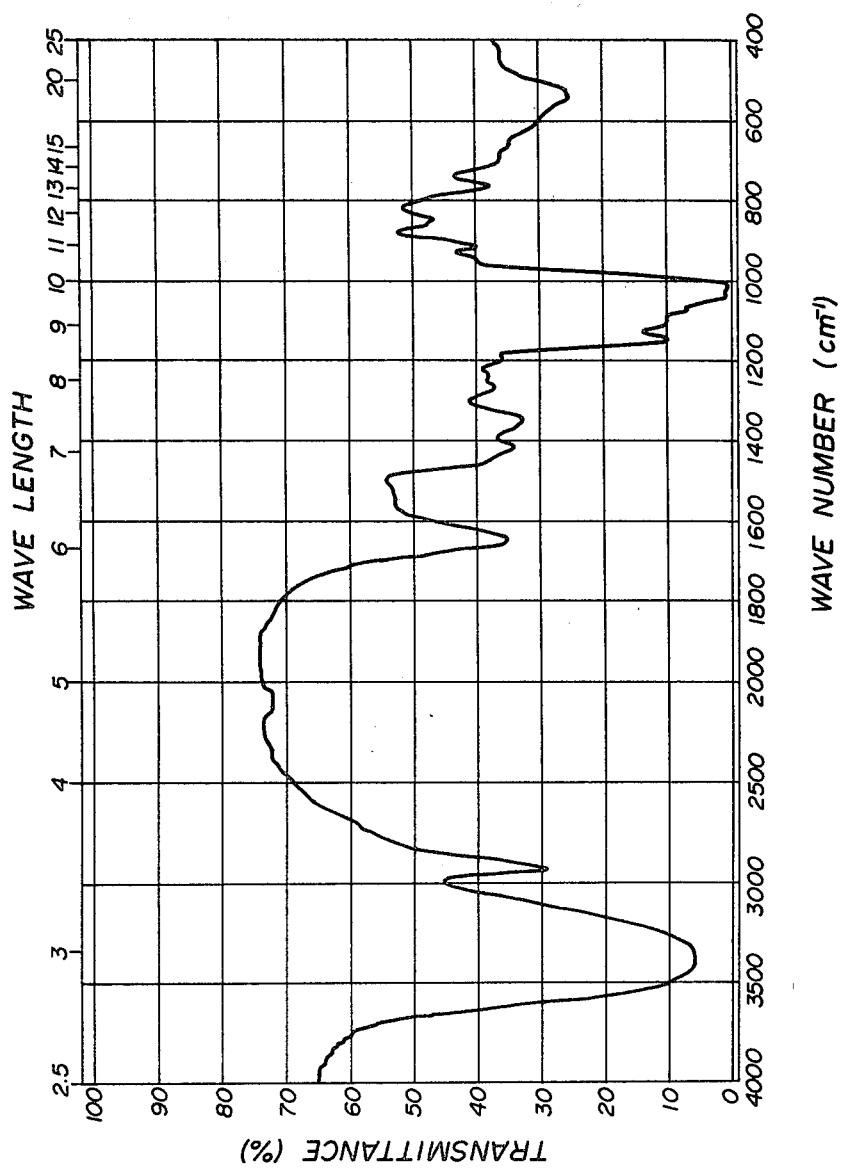
FIG. 2 is an infrared absorption spectrum of the RBS substance having antitumor activity.

The present RBS substance has an ultraviolet absorption spectrum as shown in FIG. 1 and an infrared absorption spectrum as shown in FIG. 2. From the infrared absorption spectrum and specific rotation, it is assumed that the $\alpha$-bond exists in the RBS substance.

Based upon the above described data, it is assumed that the RBS substance of this invention is a polysaccharide comprising glucose as the sugar component, which has $\alpha$-1,6-glucoside bond as the main chain with branched structure, wherein protein (or polypeptide) and aforedescribed elements are bound to the $\alpha$-glucan structure.

The polysaccharide RBS substance of this invention has antitumor activity against the tumors identified hereinafter. This has been confirmed by the following method using Sarcoma 180 and Ehrlich ascites tumors.

A group consisting of six 4-weeks-old, 20 grams female ICR-JCL mice was used for the measurement of one sample. On the 7th day from the inoculation of Sarcoma 180 ascites tumor or Ehrlich ascites tumor, the ascites were taken out with a syringe and inoculated in the abdominal cavity of mice in an amount of 0.05 ml per one mouse, i.e., $10^7$ cells. For the subsequent five days, a sample, RBS substance, dissolved in a physiological salt solution or suspended in a physiological salt solution to which 0.5 M carboxymethyl cellulose had been added in a sterilized homogenizer was administered in a given amount into the abdominal cavity. On the 7th day, the weight was measured and, thereafter, the ascites was taken out and the volume of the ascites and the tumor cell content were measured.

The total packed cell volume (hereinafter, referred to merely as "TPCV") was calculated by following equation:

TPCV (ml) = Volume of Ascites (milliliter) × Cell Ratio (%/100)

The antitumor activity was determined according to the tumor growth rate (T/C %); that is, (TPCV of test groups/TPCV of control groups) × 100

The activity is indicated as follows:

| T/C (%) | Activity |
|---------|----------|
| 0 to 10 | +++ |
| 11 to 40 | ++ |
| 41 to 65 | + |

This method is based upon the screening method for antitumor substances which was developed by Hoshi and Toruya (see FARUMASHIA, 9, 464 (1973)).

With regard to the acute toxicity of the RBS substance, when it is orally administered to male rats at the physical administration limit of 15 grams per kilogram, no death cases are observed and there is no appreciable increase in weight. Furthermore, no abnormality was observed in appearance and dissection. Therefore, the $LD_{50}$ is larger than 15 grams per kilogram and it can be concluded that the present RBS substance has no toxicity. These results are shown in Table 2.

In order to examine the antitumor effect by oral administration, $10^6$ of Sarcoma 180S cells were inoculated in the femoral muscle of an ICR-JCL mouse, the RBS substance was orally administered ten times for 10 days subsequent to the day when the inoculation was effected, and after 4 weeks, the weight of tumor was measured and compared with the control. At an administration amount of 10 milligram per kilogram, the inhibition rate was 50% or more and thus an antitumor effect was observed.

Furthermore, the examination of the direct cytocidal activity in vitro revealed that the present RBS substance has a citotoxic effect on tumor cells (SV 40—C3H-2K) in low concentrations of several γ/ml and that it has high sensitivity in comparison with normal cells (C3H-2K).

As described above, the polysaccharide RBS substance of this invention produces good results in inhibiting Sarcoma 180 ascites tumor and Ehrlich ascites tumor by the administration thereof into the abdominal cavity and Sarcoma 180 fixed type by the oral administration thereof and, furthermore, has direct cytocidal activity in vitro against tumor cells. For this substance, however, no side effects were observed.

According to this invention, the polysaccharide RBS substance having such excellent antitumor activity against the tumors specified herein can be obtained in large amounts by combinations of relatively simple procedures. Thus, this invention is of great importance in view of the production of the polysaccharide RBS substances from rice bran on a commercial scale.

The present polysaccharide RBS substance or its pharmaceutically allowable acid salt (for example, hydrochloric acid salt, sulfuric acid salt, acetic acid salt, fumalic acid salt, succinic acid salt, etc.) is admixed with vehicles such as water, physiological salt solution, polyethyleneglycol, glycelogelatin, starch, dextrin, lactose, etc. to produce antitumor agents, such as liquid medicine, pellet, tablet, powder, suppositories, etc.

The following examples are given to illustrate this invention in greater detail.

EXAMPLE 1

To 20 kilograms of rice bran was added 80 liters of distilled water, and the mixture was heated at 125° C. for 30 minutes and, thereafter, at 100° C. for 1 hour while stirring to carry out the extraction of the rice bran.

The extract so obtained was filtered and concentrated at a reduced pressure to 25 liters. Addition of 3 volumes of acetone to the concentrated extract resulted in the formation of precipitates. These precipitates were separated, dissolved in water to eliminate impurities, passed through Dowex 50 (H type) and freeze-dried to thereby obtain 378 grams of white-grey nonhygroscopic powder.

The analytical values and the results of the antitumor activity against the specified tumors of the so obtained polysaccharide are shown in Tables 1 and 2 respectively.

EXAMPLE 2

Rice bran was passed through a 300 mesh screen to remove crushed rice and the like. After washing of 20 kilograms of the thus obtained fine powder with 200 liters of distilled water, 30 liters of distilled water was added thereto, and the resulting mixture was heated at 120° C. for 1 hour and then at 100° C. for 5 hours while stirring to carry out the extraction of the rice bran.

The extract obtained was filtered and the filtrate so obtained was concentrated at reduced pressure. Thereafter, ethanol was added to the concentrate so that the concentration of ethanol was 40% by volume, and the resulting mixture was subjected to centrifugation to obtain precipitates. These precipitates were dissolved in water and freeze-dried to obtain 1,310 grams of white-grey powder.

The analytical values and the results of the antitumor activity against the specified tumors of the above obtained polysaccharide are shown in Tables 1 and 2 respectively.

EXAMPLE 3

A filtrate obtained by the extraction of the same starting material as used in Example 2 under the same conditions as in Example 2 was concentrated at reduced pressure. Thereafter, ethanol was added to the concentrate so that the concentration of ethanol was 30% by volume. By centrifugation of the mixture, precipitates were otained, and they were dissolved in water.

To this aqueous solution was added 600 milligrams of amylase (crystalline α-amylase, produced by Nagase Sangyo Co., Ltd.) and reacted at 75° C. for 18 hours. The reaction product was maintained at 100° C. for 1 hour and filtered. By adding ethanol to the filtrate so that the concentration of ethanol by 50% was volume, precipitates were obtained. These precipitates were again dissolved in water, dialyzed against running water for 3 days to remove low molecular substances, filtered and freeze-dried to obtain 394 grams of white-grey powder.

The analytical values and the results of the antitumor activity against the specified tumors of the above obtained polysaccharide are shown in Tables 1 and 2 respectively.

EXAMPLE 4

Precipitates obtained from a mixture having an ethanol concentration of 30% by volume in the same manner as in Example 3 were dissolved in water and maintained at 47° C. To this aqueous solution was added 600 milligrams of proteolytic enzyme (pronase E, produced by Kaken Kagaku Co., Ltd.) and reacted for 24 hours. After the heating of the reaction mixture at 100° C. for 1 hour, by adding ethanol so that the concentration of ethanol was 50% by volume, precipitates were obtained. These precipitates were again dissolved in water, subjected twice to one day-dialysis using a 30 times amount of distilled water to remove low molecular substances, filtered and freeze-dried to thereby obtain 374 grams of white-grey powder.

The analytical values and the results of the antitumor activity against the specified tumors of the above obtained polysaccharide are shown in Tables 1 and 2 respectively.

EXAMPLE 5

A reaction product obtained in the same manner as in Example 4 was dialyzed against running water for 1 day and after adding trichloroacetate until the concentration reached 4% (w/v), it was stored in a refrigerator overnight. After removal of precipitates, ethanol was added until the concentration reached 80% to thereby obtain precipitates. This procedure was repeated twice. Thereafter, the precipitates were dialyzed using a 100 times amount of distilled water for 2 days and freeze-dried to thereby obtain 164 grams of a white-grey spongy substance.

The analytical values and the results of the antitumor activity against the specified tumors of the above obtained polysaccharide are shown in Tables 1 and 2 respectively.

EXAMPLE 6

To 20 kilograms of the rice bran was added 80 liters of distilled water, and the resulting mixture was heated at 110° C. for 2 hours and then at 100° C. for 3 hours with stirring to carry out the extraction of the rice bran.

The extract was filtered and concentrated under reduced pressure. Ethanol was added thereto so that the concentration of ethanol was 30% (v/v) to obtain precipitates. These precipitates were collected and again suspended in distilled water. To this suspension was added crystalline α-amylase in an amount of 1/1000 based on the amount of the precipitates and reacted at 75°–80° C. for 24 hours. Thereafter, pronase E was added in an amount of 1/1000 based on the amount of the precipitates and reacted at 45° C. for 24 hours.

After the completion of the reaction, the reaction solution was maintained at 100° C. for 1 hour and, thereafter, it was cooled to ambient temperature. When the solution was subjected to ultrafiltration using an ultrafilter membrane (UK-200, produced by Toyo Kagaku Sangyo Co., Ltd.) having a fractional molecular weight of 200,000 and the remaining solution was freeze-dried, 205 grams of white-grey powder was obtained.

The analytical values and the results of the antitumor activity against the specified tumors of the above obtained polysaccharide are shown in Tables 1 and 2 respectively.

EXAMPLE 7

The filtrate obtained by ultrafiltration in Example 6 was further subjected to ultrafiltration using an ultrafilter membrane (UK-50, produced by Toyo Kagaku Sangyo Co., Ltd.) having a fractional molecular weight of 50,000, and on freeze-drying the remaining solution, 101 grams of white-grey powder was obtained.

The analytical values and the results of the antitumor activity against the specified tumors of the above obtained polysaccharide are shown in Tables 1 and 2 respectively.

EXAMPLE 8

75% Acetone precipitates obtained in the same manner as in Example 1 were separated and then dissolved in water. After removal of insoluble substances by centrifugation (18,000 G × 30 minutes), the supernatant was filtered through a membrane filter having a pore diameter of 1.0μ, and the filtrate obtained was further filtered through a membrane filter having a pore diameter of 0.45μ. On freeze-drying the remaining solution, 8.3 grams of white-grey powder was obtained.

The analytical values and the results of the antitumor activity of the polysaccharide obtained are shown in Tables 1 and 2 respectively.

EXAMPLE 9

The filtrate obtained in Example 8 was filtered through a membrane filter having a pore diameter of 0.1μ and the obtained filtrate was filtered through an ultrafiltration membrane having a fractional molecular weight of 200,000. Thereafter, on freeze-drying the remaining solution, 368.4 grams of white-grey powder was obtained.

The analytical values and the results of the antitumor activity against the specified tumors of the above obtained polysaccharide are shown in Tables 1 and 2 respectively.

EXAMPLE 10

In the same manner as in Example 6 except that ammonium sulfate having a concentration of 35% (w/w) was used in place of ethanol, 190 grams of white-grey powder was obtained.

The analytical values and the results of the antitumor activity against the specified tumors of the above obtained polysaccharide are shown in Tables 1 and 2 respectively.

EXAMPLE 11

To 10 kilograms of rice bran was added 50 liters of distilled water. The mixture obtained was heated with stirring at 100° C. for 5 hours to extract and the extract was then subjected to centrifugation to obtain 46 liters of a supernatant liquid which was then concentrated at reduced pressure to 20 liters. To the concentrated supernatant liquid was added 200 milligrams of crystalline α-amylase, and the resulting mixture was maintained at 70° C. for 20 hours and then heated up to 100° C. Thereafter, the mixture was subjected to centrifugation to obtain 18.5 liters of a supernatant liquid. To this supernatant liquid was added ethanol so that the concentration of ethanol was 35%, and the formed precipitates were separated and freeze-dried to obtain 238 grams of yellow-white powder.

The analytical values and the results of the antitumor activity against the specified tumors of the above obtained polysaccharide are shown in Tables 1 and 2 respectively.

EXAMPLE 12

Ten kilograms of rice bran was subjected to delipid treatment under reflux by use of 50 liters of hexane and dried. The thus obtained rice bran was treated in the same manner as in Example 11 to thereby obtain 245 grams of yellow-white powder. This powder was dissolved in 1 liter of water and subjected to centrifugation. On freeze-drying the supernatant liquid so obtained, 165 grams of yellow-white powder was obtained.

The analytical values and the results of the antitumor activity against the specified tumors of the above obtained polysaccharide are shown in Tables 1 and 2 respectively.

EXAMPLE 13

To 3 kilograms of rice bran was added 20 liters of water, and the resulting mixture was heated at 120° C. for 2 hours while stirring to carry out the extraction of the rice bran.

The extract was concentrated at reduced pressure. To 5 liters of the concentrated solution was added 0.3 gram of crystalline α-amylase (produced by Nagase Sangyo Co., Ltd.). The resulting mixture was kept at 60° C. for 5 hours, then heated up to 100° C. Subsequently, the mixture was subjected to centrifugation to obtain 4.9 liters of a supernatant liquid to which was then added ethanol so that the concentration of ethanol was 40%. The precipitates formed were separated and collected. Thereafter, these precipitates were freeze-dried to obtain 88 grams of light yellowish brown powder.

The analytical values and the results of the antitumor activity against the specified tumors of the above obtained polysaccharide are shown in Tables 1 and 2 respectively.

EXAMPLE 14

Twenty kilograms of rice bran on the market was passed through a 30 mesh screen to remove impurities such as pulverized rice and it was then washed with 100 liters of water which had been treated with an ion exchange resin. To the so washed rice bran was added 50 liters of distilled water, and the resulting mixture was heated under pressure at 110° C. for 3 hours while stirring to carry out the extraction of the rice bran and it was then filtered.

The so obtained filtrate was concentrated at reduced pressure and furthermore subjected to centrifugation to obtain 10 liters of a supernatant liquid. To this supernatant liquid was added 250 milligrams of crystalline α-amylase, and the mixture was reacted at 65° C. for 24 hours and then heated up to 100° C. Thereafter, ethanol was added thereto so that the concentration of ethanol was 30% and the formed precipitates were separated and collected by centrifugation.

These precipitates were dissolved in 3 liters of water and then subjected to centrifugation to thereby obtain a supernatant liquid. This liquid was concentrated at reduced pressure to 1 liter and, furthermore, subjected to centrifugation to thereby obtain a supernatant liquid. On freeze-drying the so obtained liquid, 411 grams of light yellow-brown powder was obtained.

EXAMPLE 15

Twenty grams of the powder as obtained in Example 14 was dissolved in 500 milliliters of water and the solution so obtained was subjected to centrifugation to obtain a supernatant liquid. 480 milliliters of the supernatant liquid was treated successively with a cation exchange gel, CM Sephalose (produced by Pharmacia Fine Chemicals, Ltd.), and an anion exchange resin, DEAE Sephalose (produced by Pharmacia Fine Chemicals, Ltd.). A portion which had not been adsorbed was freeze-dried to thereby obtain 14 grams of white powder.

The analytical values and the results of the antitumor activity against the specified tumors of the above obtained polysaccharide are shown in Tables 1 and 2 respectively.

EXAMPLE 16

Twenty grams of the powder as obtained in Example 14 was dissolved in 500 milliliters of water, and 5 grams of active carbon was then added thereto. After 30 minutes, the mixture was subjected to centrifugation to obtain a supernatant liquid. This liquid was freeze-dried to obtain 18 grams of white powder.

The analytical values and the results of the antitumor activity against the specified tumors of the above obtained polysaccharide are shown in Tables 1 and 2 respectively.

EXAMPLE 17

Fifty grams of the powder as obtained in Example 14 was dissolved in 1 liter of water and subjected to centrifugation to obtain a supernatant liquid. This liquid was subjected to gel filtration using Sephalose 6B (produced by Pharmacia Fine Chemicals, Ltd.). The void-volume fraction was freeze-dried to obtain 48 grams of white powder.

The analytical values and the results of the antitumor activity against the specified tumors of the above obtained polysaccharide are shown in Tables 1 and 2 respectively.

TABLE 1

Analysis of Polysaccharide RBS Substance

| Example | Elemental Analysis (%) | | | General Analysis (%) | | | | |
|---|---|---|---|---|---|---|---|---|
| | C | H | N | Glucide* | Crude Protein** | Crude Lipid*** | Crude Cellulose | Crude Ash |
| 1 | 39.90 | 6.53 | 0.49 | 87.2 | 4.3 | 0.4 | 0 | 8.0 |
| 2 | 43.49 | 6.79 | 0.85 | 83.7 | 6.2 | 1.7 | 0.2 | 7.7 |
| 3 | 40.26 | 6.51 | 1.00 | 85.8 | 7.1 | 0.5 | 0 | 7.1 |
| 4 | 39.63 | 6.47 | 0.96 | 85.6 | 7.0 | 0.3 | 0 | 6.8 |
| 5 | 39.71 | 6.30 | 0.90 | 86.1 | 6.8 | 0.2 | 0 | 6.5 |
| 6 | 40.73 | 6.29 | 0.79 | 84.6 | 7.1 | 0.8 | 0 | 7.6 |
| 7 | 39.63 | 6.15 | 0.68 | 84.2 | 6.6 | 0.6 | 0 | 7.2 |
| 8 | 39.51 | 6.13 | 0.76 | 86.4 | 6.7 | 0.5 | 0 | 6.4 |
| 9 | 37.97 | 5.91 | 0.34 | 87.0 | 3.7 | 0.3 | 0 | 6.0 |
| 10 | 40.55 | 6.31 | 0.75 | 85.0 | 6.9 | 0.7 | 0 | 6.8 |
| 11 | 43.02 | 6.80 | 0.79 | 84.5 | 5.7 | 0.2 | 0 | 7.3 |
| 12 | 40.75 | 6.39 | 0.44 | 87.3 | 4.3 | 0 | 0 | 4.2 |
| 13 | 41.26 | 6.47 | 0.32 | 88.6 | 4.0 | 0 | 0 | 3.9 |
| 14 | 40.03 | 6.11 | 0.23 | 90.1 | 3.8 | 0 | 0 | 2.5 |
| 15 | 40.67 | 6.28 | 0.28 | 89.8 | 4.1 | 0 | 0 | 2.0 |
| 16 | 38.98 | 6.17 | 0.22 | 90.2 | 3.6 | 0 | 0 | 2.4 |
| 17 | 39.75 | 6.13 | 0.18 | 92.5 | 3.5 | 0 | 0 | 2.5 |

*According to phenol-sulfuric acid method
**According to microbiuret method
***According to chloroform-methanol extraction method

TABLE 2

Antitumor Activity of Polysaccharide RBS Substance

| Example | Dosage (mg/Kg) | Antitumor activity against Sarcoma 180 ascites tumor | Antitumor activity against Ehrlich ascites tumor |
| --- | --- | --- | --- |
| 1 | 100 | ++ | + |
| 2 | 100 | ++ | ++ |
| 3 | 100 | +++ | +++ |
| 4 | 100 | +++ | +++ |
| 5 | 100 | +++ | +++ |
| 6 | 100 | +++ | +++ |
| 7 | 100 | + | + |
| 8 | 100 | ++ | ++ |
| 9 | 100 | +++ | ++ |
| 10 | 100 | +++ | ++ |
| 11 | 100 | ++ | ++ |
| 12 | 100 | +++ | ++ |
| 13 | 100 | +++ | ++ |
| 14 | 100 | +++ | +++ |
| 15 | 100 | ++ | ++ |
| 16 | 100 | +++ | ++ |
| 17 | 100 | +++ | ++ |

What is claimed is:

1. A polysaccharide RBS substance and pharmaceutically acceptable addition salts thereof (1) having the following properties:

it does not pass through a semipermeable membrane;

it is insoluble in alcohol, acetone, hexane, benzene, ethyl acetate, dimethylsulfoxide, ligroin, carbon tetrachloride, chloroform and ether, and is soluble or highly soluble in water;

a 1% aqueous solution or suspension is neutral or slightly acidic;

it reacts positively in the following reactions: the Molisch reaction, the anthrone-sulfuric acid reaction, the tryptophane-sulfuric acid reaction, the crystein-sulfuric acid reaction, the chromotrope-sulfuric acid reaction, the phenol-sulfuric acid reaction, the carbazole-sulfuric acid reaction, the biuret reaction, the ninhydrin reaction and the Lowry-Folin reaction; and negatively in the Elson-Morgan reaction and the starch-iodine reaction;

it has the ultraviolet absorption spectrum depicted in FIG. 1 and the infrared absorption spectrum depicted in FIG. 2; and (2) containing glucose units as the sugar component, said glucose units being bonded by $\alpha$-1,6 glucoside bonds as the main chain and said main chain is branched.

2. A pharmaceutical composition effective in inhibiting the growth of Sarcoma 180 ascites tumors, Erlich ascites tumors, and tumor cells (SV 40-transformed C3H-2K cells) consisting essentially of polysaccharide RBS substance and pharmaceutically acceptable acid-addition salts thereof in a pharmaceutically effective amount, and a pharmaceutically acceptable vehicle, said polysaccharide RBS substance (1) having the following properties:

it does not pass through a semipermeable membrane;

it is insoluble in alcohol, acetone, hexane, benzene, ethyl acetate, dimethylsulfoxide, ligroin, carbon tetrachloride, chloroform and ether, and is soluble or highly soluble in water;

a 1% aqueous solution or suspension is neutral or slightly acidic;

it reacts positively in the following reactions: the Molisch reaction, the anthrone-sulfuric acid reaction, the tryptophane-sulfuric acid reaction, the crystein-sulfuric acid reaction, the chromotrope-sulfuric acid reaction, the phenol-sulfuric acid reaction, the carbazole-sulfuric acid reaction, the biuret reaction, the ninhydrin reaction and the Lowry-Folin reaction; and negatively in the Elson-Morgan reaction and the starch-iodine reaction;

it has the ultraviolet absorption spectrum depicted in FIG. 1 and the infrared absorption spectrum depicted in FIG. 2; and (2) containing glucose units as the sugar component, said glucose units being bonded by $\alpha$-1,6-glucoside bonds as the main chain and said main chain is branched.

* * * * *